(12) United States Patent
Fujiwara et al.

(10) Patent No.: US 9,704,242 B2
(45) Date of Patent: Jul. 11, 2017

(54) DYNAMIC IMAGE PROCESSING APPARATUS AND COMPUTER-READABLE RECORDING MEDIUM FOR PROVIDING DIAGNOSIS SUPPORT

(71) Applicant: KONICA MINOLTA, INC., Tokyo (JP)

(72) Inventors: Koichi Fujiwara, Osaka (JP); Osamu Toyama, Kakogawa (JP); Hiroshi Yamato, Amagasaki (JP); Kenta Shimamura, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/643,532

(22) Filed: Mar. 10, 2015

(65) Prior Publication Data

US 2015/0262359 A1 Sep. 17, 2015

(30) Foreign Application Priority Data

Mar. 17, 2014 (JP) ................................ 2014-053210

(51) Int. Cl.
*G06K 9/00* (2006.01)
*G06T 7/00* (2017.01)
(Continued)

(52) U.S. Cl.
CPC ............ *G06T 7/0016* (2013.01); *A61B 6/486* (2013.01); *A61B 6/5217* (2013.01); *A61B 8/08* (2013.01);
(Continued)

(58) Field of Classification Search
None
See application file for complete search history.

(56) References Cited

U.S. PATENT DOCUMENTS 5,848,198 A * 12/1998 Penn .................. G06T 7/0012
382/276
9,058,650 B2 * 6/2015 El-Hilo .................. G06K 9/00
(Continued)

FOREIGN PATENT DOCUMENTS

JP 2004-312434 11/2004
JP 2004312434 * 11/2004

OTHER PUBLICATIONS

JP2004-312434, machine translation (attached).*
(Continued)

*Primary Examiner* — Vu Le
*Assistant Examiner* — Samah Beg
(74) *Attorney, Agent, or Firm* — Brinks Gilson & Lione

(57) ABSTRACT

An image processing apparatus includes: a storage unit configured to store corresponding information in which one or more images of one or more frame images included in a dynamic image and one or more calculation middle images generated from two or more frame images included in the dynamic image relative to the single pixel region for each pixel region including one or more pixels in a calculation result image having the statistic obtained by the calculation for a medical dynamic image as each pixel value; a specification unit configured to specify the one or more pixel regions in the calculation result image; and a determination unit configured to determine one or more output images based on one or more images corresponding to the one or more pixel regions specified by the specification unit in the corresponding information.

14 Claims, 13 Drawing Sheets

(51) Int. Cl.
*A61B 6/00* (2006.01)
*A61B 8/08* (2006.01)

(52) U.S. Cl.
CPC ... *A61B 8/5223* (2013.01); *G06T 2207/10081* (2013.01); *G06T 2207/10088* (2013.01); *G06T 2207/10116* (2013.01); *G06T 2207/10132* (2013.01); *G06T 2207/30061* (2013.01)

(56) References Cited

U.S. PATENT DOCUMENTS

| | | | | |
|---|---|---|---|---|
| 9,237,877 | B2* | 1/2016 | Noji | A61B 5/08 |
| 2003/0190064 | A1* | 10/2003 | Inoue | A61B 6/02 |
| | | | | 382/128 |
| 2003/0210813 | A1* | 11/2003 | Oosawa | G06T 7/0012 |
| | | | | 382/130 |
| 2005/0041837 | A1* | 2/2005 | Fan | G06T 7/0012 |
| | | | | 382/103 |
| 2005/0265606 | A1* | 12/2005 | Nakamura | G06T 7/0012 |
| | | | | 382/218 |
| 2006/0045370 | A1* | 3/2006 | Blaffert | G06K 9/469 |
| | | | | 382/254 |
| 2006/0239530 | A1* | 10/2006 | Oosawa | G06T 7/0012 |
| | | | | 382/130 |
| 2007/0110307 | A1* | 5/2007 | Sato | G06T 5/50 |
| | | | | 382/169 |
| 2010/0246925 | A1* | 9/2010 | Nagatsuka | A61B 5/08 |
| | | | | 382/132 |
| 2011/0075907 | A1* | 3/2011 | Nakanishi | A61B 6/032 |
| | | | | 382/131 |
| 2012/0130238 | A1* | 5/2012 | Muraoka | A61B 6/4233 |
| | | | | 600/436 |
| 2012/0300904 | A1* | 11/2012 | Shimada | A61B 6/4291 |
| | | | | 378/62 |
| 2013/0156158 | A1* | 6/2013 | Noji | A61B 5/08 |
| | | | | 378/62 |
| 2013/0156267 | A1* | 6/2013 | Muraoka | A61B 6/507 |
| | | | | 382/103 |
| 2013/0331725 | A1* | 12/2013 | Noji | A61B 6/5217 |
| | | | | 600/534 |
| 2014/0210973 | A1* | 7/2014 | Takahashi | A61B 1/04 |
| | | | | 348/65 |
| 2015/0042677 | A1* | 2/2015 | Shimamura | A61B 6/4233 |
| | | | | 345/632 |
| 2015/0065817 | A1* | 3/2015 | Noji | A61B 5/113 |
| | | | | 600/301 |
| 2015/0163479 | A1* | 6/2015 | Inoue | G06T 5/50 |
| | | | | 348/47 |
| 2015/0254836 | A1* | 9/2015 | Sako | A61B 1/00009 |
| | | | | 382/128 |
| 2015/0254841 | A1* | 9/2015 | Fujiwara | G06T 7/0012 |
| | | | | 378/62 |
| 2015/0262359 | A1* | 9/2015 | Fujiwara | G06T 7/0016 |
| | | | | 382/132 |
| 2015/0310625 | A1* | 10/2015 | Shimamura | A61B 6/4233 |
| | | | | 382/132 |
| 2016/0055649 | A1* | 2/2016 | Peret | G01F 1/661 |
| | | | | 348/135 |
| 2016/0104283 | A1* | 4/2016 | Fujiwara | G06T 7/0016 |
| | | | | 382/132 |
| 2016/0120491 | A1* | 5/2016 | Shimamura | A61B 6/463 |
| | | | | 348/333.05 |
| 2016/0210747 | A1* | 7/2016 | Hay | G06T 7/11 |

OTHER PUBLICATIONS

Office Action mailed on Mar. 28, 2017 regarding corresponding Chinese patent application 201510111821.7, eleven (11) pages, including English-language translation of Office Action, thirteen (13) pages.

* cited by examiner

DYNAMIC IMAGE PROCESSING APPARATUS AND COMPUTER-READABLE RECORDING MEDIUM FOR PROVIDING DIAGNOSIS SUPPORT

The entire disclosure of Japanese Patent Application No. 2014-053210 filed on Mar. 17, 2014 including description, claims, drawings, and abstract are incorporated herein by reference in its entirety.

BACKGROUND OF THE INVENTION

Field of the Invention

The present invention relates to an image processing apparatus for performing processing for a dynamic image and a computer-readable recording medium.

Description of the Related Art

In the medical field, a technique has been known in which a dynamic image for capturing an object part in a body is obtained by taking the x-ray by using a semiconductor image sensor such as a flat panel detector (FPD). For example, various statistics are calculated regarding a change of brightness and the like in the dynamic image (referred to as a x-ray dynamic image) obtained by taking the x-ray by using the FPD and the like, and the display is performed based on the statistic. Accordingly, when performing the diagnosis, the doctor can easily grasp a functional state of the object part. That is, information which is useful for the diagnosis by the doctor is provided, and the diagnosis by the doctor may be supported.

As this technique, for example, a technique has been proposed in which one image (referred to as an analysis result image) having the representative value as the pixel value is generated and displayed regarding the respective pixels of a plurality of difference images between images temporally adjacent to each other in the x-ray dynamic image (for example, JP 2004-312434 and the like). Here, for example, any one of the maximum value, the minimum value, the average value, and the median value may be employed as a representative value.

However, in the technique described in JP 2004-312434 A, a tendency regarding the function of a specific part may be grasped from the analysis result image. However, it is difficult to grasp detailed information such that what kind of abnormality occurs in the function of the specific part and when the abnormality occurs. Therefore, it is difficult to say that the diagnosis regarding the specific part can be sufficiently supported.

This problem generally occurs in a technique for supporting the diagnosis by using the dynamic image which captures the object part of the living body without the limitation to the technique for supporting the diagnosis by using the x-ray dynamic image.

SUMMARY OF THE INVENTION

The present invention has been made in view of the above-described problems, and an object thereof is to provide a technique for easily obtaining detailed information regarding an analysis result of a dynamic image for capturing an object part of a living body.

To achieve the abovementioned object, according to an aspect, an image processing apparatus reflecting one aspect of the present invention comprises a storage unit configured to store corresponding information in which one or more images of one or more frame images included in a dynamic image and one or more calculation middle images generated from two or more frame images included in the dynamic image in which a pixel value is employed when a statistic regarding a single pixel region is obtained in the calculation, relative to the single pixel region for each pixel region including one or more pixels in a calculation result image having the statistic obtained by the calculation for a medical dynamic image as each pixel value, a specification unit configured to specify the one or more pixel regions in the calculation result image, and a determination unit configured to determine one or more output images based on one or more images corresponding to the one or more pixel regions specified by the specification unit in the corresponding information.

To achieve the abovementioned object, according to an aspect, a non-transitory recording medium storing a computer readable program reflecting one aspect of the present invention causes the image processing apparatus to function as the image processing apparatus according to the first aspect by executing the program to be recorded by a processor included in the image processing apparatus.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Figure 3:
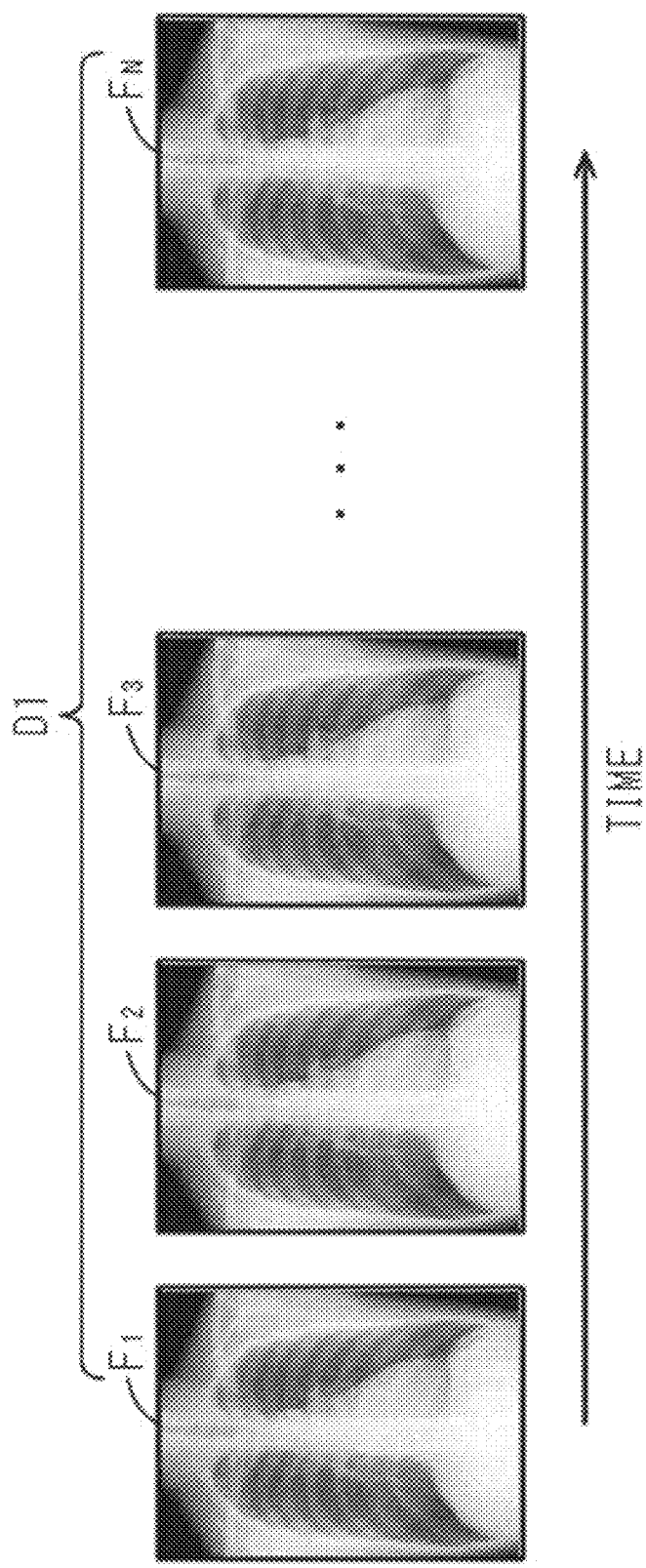
FIG. 3 is a diagram of a plurality of exemplary frame images included in a dynamic image.
Figure 6:
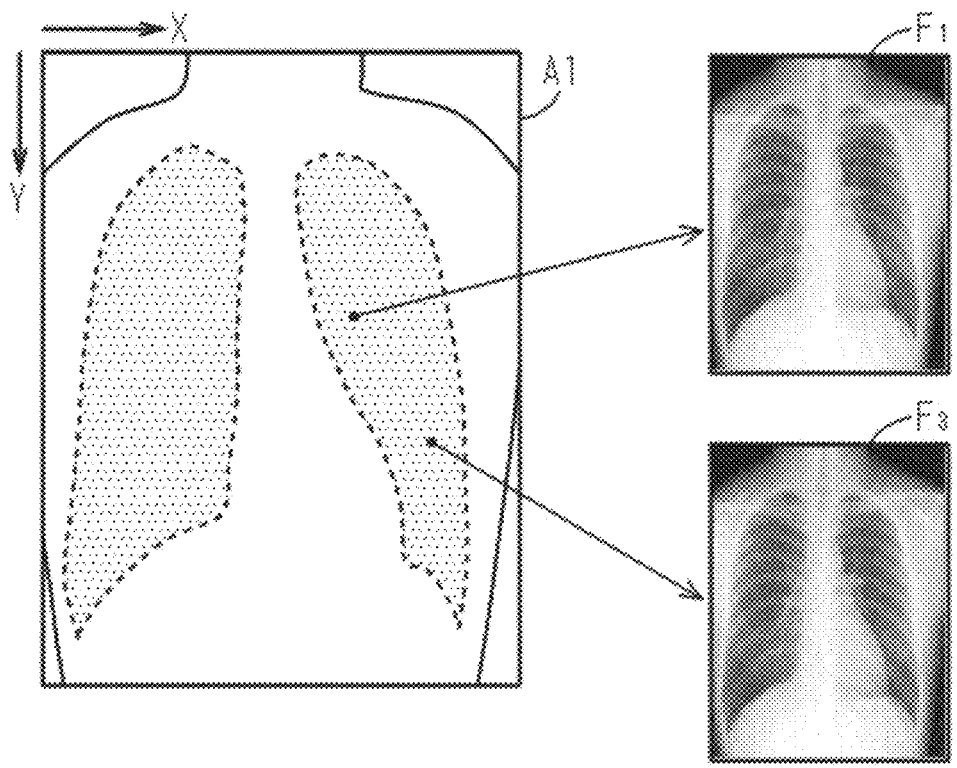
FIG. 6 is a diagram to describe exemplary corresponding information.
Figure 7:
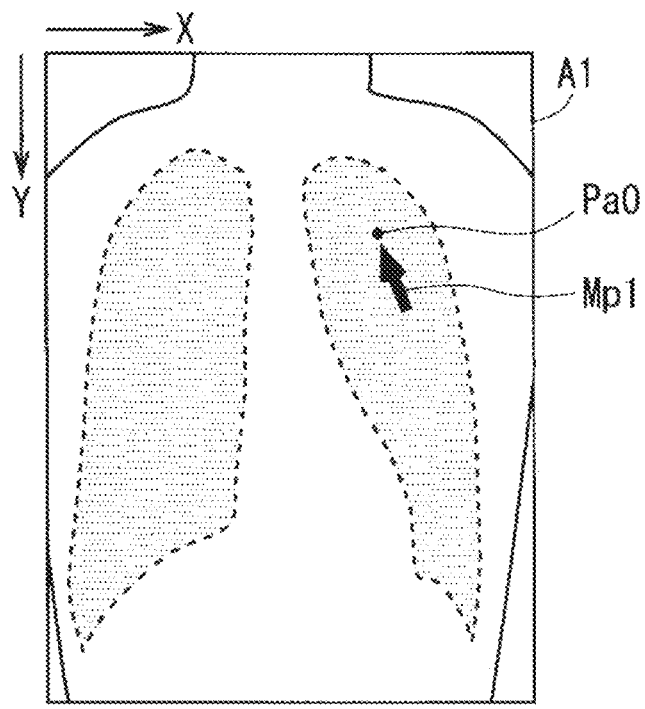
FIG. 7 is a diagram of an exemplary first specifying mode of a pixel region in a calculation result image.
Figure 8:
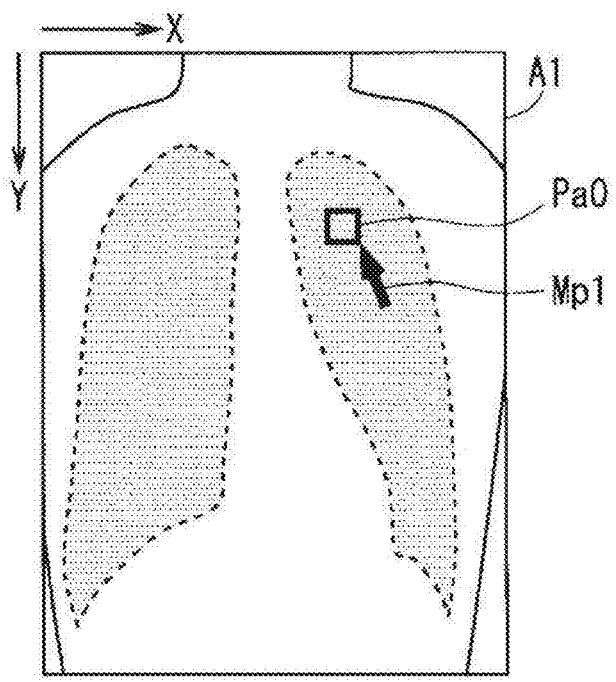
FIG. 8 is a diagram of an exemplary second specifying mode of a pixel region in a calculation result image.
Figure 14:
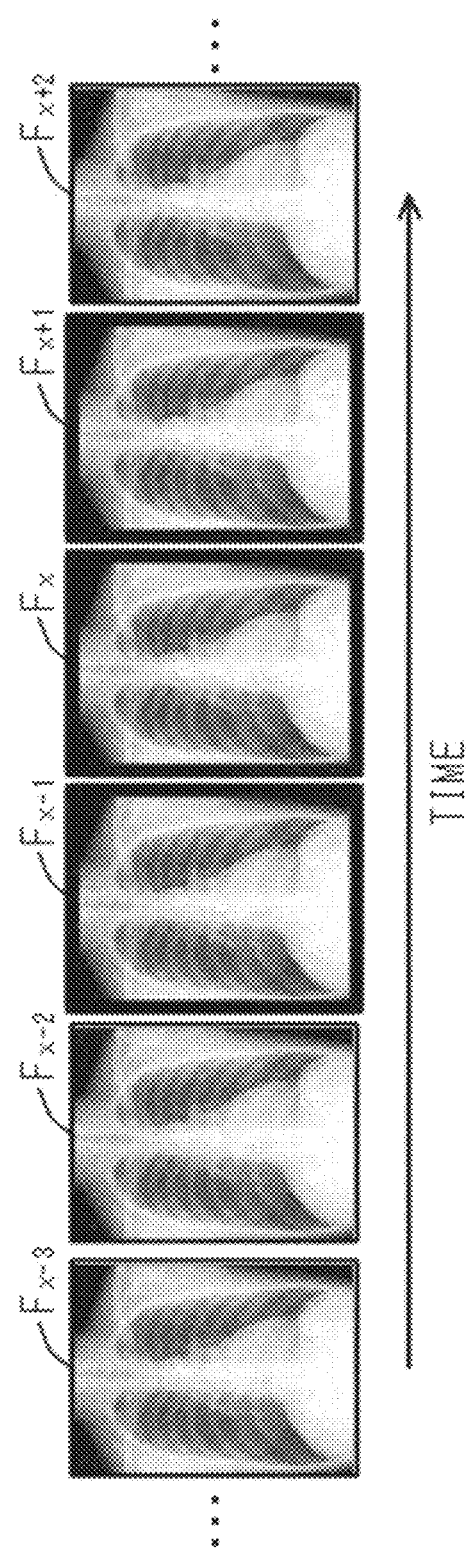
FIG. 14 is a diagram of a display example for displaying an output image in a moving image mode.
Figure 17:
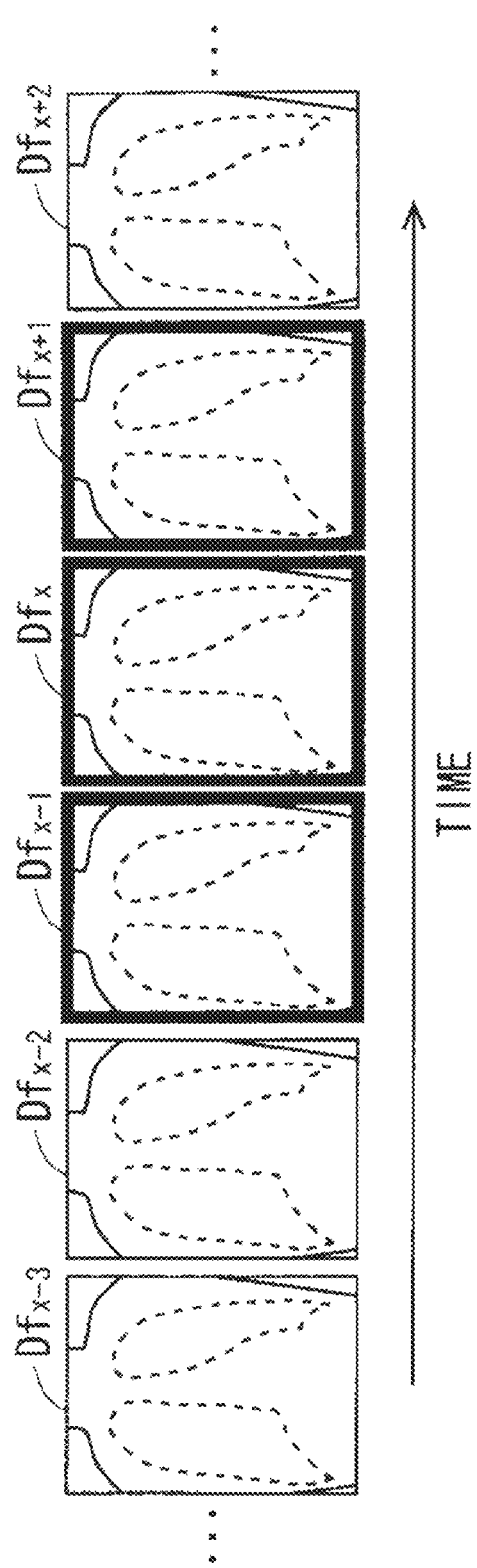
FIG. 17 is a diagram of another display example for displaying an output image in a moving image mode.

Hereinafter, an embodiment and a modification of the present invention will be described with reference to the drawings. However, the scope of the invention is not limited to the illustrated examples. Regarding the drawings, parts having similar components and functions are respectively denoted with the same reference numerals. The overlapping descriptions will be omitted below. Also, the drawings are schematically illustrated, and a reciprocal relationship between the sizes and positions of the images respectively illustrated in different drawings is not necessarily accurate and may be appropriately changed. In FIGS. 6 to 8, a XY coordinate system is illustrated in which an origin is positioned at upper left of the image, the right direction is a X direction, and the downward direction is a Y direction. In FIGS. 3, 14, and 17, a time axis corresponding to a photographing time of the frame image included in the dynamic image is illustrated.

<(1) Outline Of Image Processing Apparatus>

Figure 1:
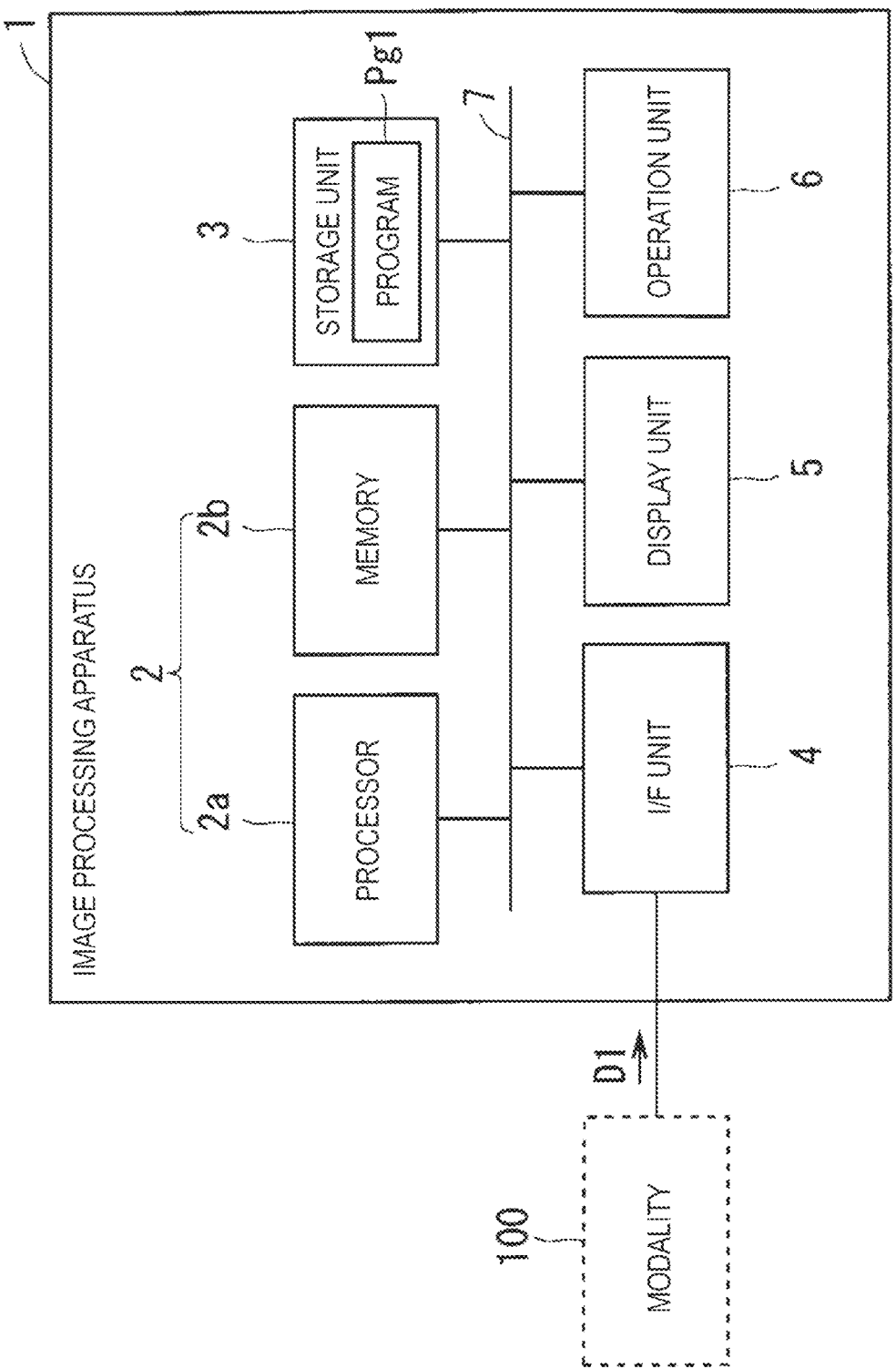
FIG. 1 is a block diagram of an exemplary structure of an image processing apparatus according to one embodiment.

FIG. 1 is a block diagram of an exemplary structure of an image processing apparatus 1 according to one embodiment. As illustrated in FIG. 1, the image processing apparatus 1 has a structure similar to a general computer in which a controller 2, a storage unit 3, an interface (I/F) unit 4, a display unit 5, and an operation unit 6 are connected to a bus line 7.

For example, the controller 2 includes a processor 2a which is a CPU and the like, a memory 2b which is a volatile RAM and the like. The processor 2a realizes processing for supporting the diagnosis (also referred to as diagnosis support processing) by using a medical dynamic image by a doctor by reading a program Pg1 stored in the storage unit 3 and executing various processing according to the program Pg1. That is, a function of the image processing apparatus 1 for performing the diagnosis support processing is realized by executing the program Pg1 by the processor 2a.

The storage unit 3 includes a non-volatile semiconductor memory, a hard disk, or the like and stores the program Pg1 and various data. The various data may include data indicating a parameter and the like necessary for performing the processing according to the program Pg1, data which is at least temporarily generated as a result of the calculation, and the like.

The I/F unit 4 is connected to various devices arranged outside the image processing apparatus 1 via a communication line so as to transmit/receive the data. For example, the I/F unit 4 obtains a medical image (referred to as a dynamic image) D1 which captures the movement of an object part in a living body from a modality 100. The modality 100 is connected to the I/F unit 4 so as to transfer/receive the data. Here, for example, the modality 100 may include a medical imaging apparatus typified by a CT, a MRI, an ultrasonic diagnosis apparatus, and the like. The modality 100 takes an x-ray by using a FPD in the present embodiment. The living body may include, for example, various animals including humans and the like. Also, the object part in the body may include, for example, various organs such as a lung field. The living body is the human and the object part is the lung field in the present embodiment.

The display unit 5 visually outputs various image data. The display unit 5 includes various display apparatuses such as a liquid crystal display (LCD).

The operation unit 6 includes a pointing device and the like such as a keyboard and a mouse. The operation unit 6 outputs a signal (referred to as an instruction signal) generated by the operation relative to the keyboard, the mouse, and the like to the controller 2. A structure such as a touch screen may be employed as the operation unit 6

<(2) Functional Structure According To Diagnosis Support Processing>

In the diagnosis support processing, an image (referred to as a calculation result image) A1 (FIG. 5) is generated. The image has a statistic obtained by the calculation for the medical dynamic image D1 (FIG. 3) as a pixel value. At this time, one or more images in which the pixel value is employed when the statistic is obtained correspond to the respective pixel regions of the calculation result image A1. An output image is determined based on one or more images corresponding to one or more pixel regions in response to specifying the one or more pixel regions in the calculation result image A1 by the doctor as a user.

Accordingly, for example, in the diagnosis by using the medical dynamic image D1 by the doctor, the calculation result image A1 as an analysis result and the image employed when the statistic, which gathers attention in the calculation result image A1, is obtained may be displayed together. That is, detailed information can be easily obtained when the dynamic image D1 which captures the object part of the living body is analyzed. As a result, the diagnosis regarding the object part is supported, and inappropriate diagnosis hardly occurs.

For example, in the lung field as the object part, a structure such as an alveolus is expanded/contracted associated with breathing. Therefore, when the dynamic image, which is obtained by taking the x-ray by using FPD, of the lung field in the state where the breathing is performed, the transmittance of the x-ray changes according to the expansion and the contraction of the structure in the abovementioned lung field. The change of the transmittance of the x-ray causes a change of the pixel density (pixel value) in the dynamic image. However, when the amounts of the expansion and the contraction of the alveolus and the like become small by some kinds of diseases, the change of the pixel value in the dynamic image becomes small.

In the present embodiment, an example will be described in which a function of the lung field is analyzed by obtaining statistics according to a difference between the pixel values of the respective pixels of frame images of which the photographing orders are next to each other in the dynamic image D1.

Figure 2:
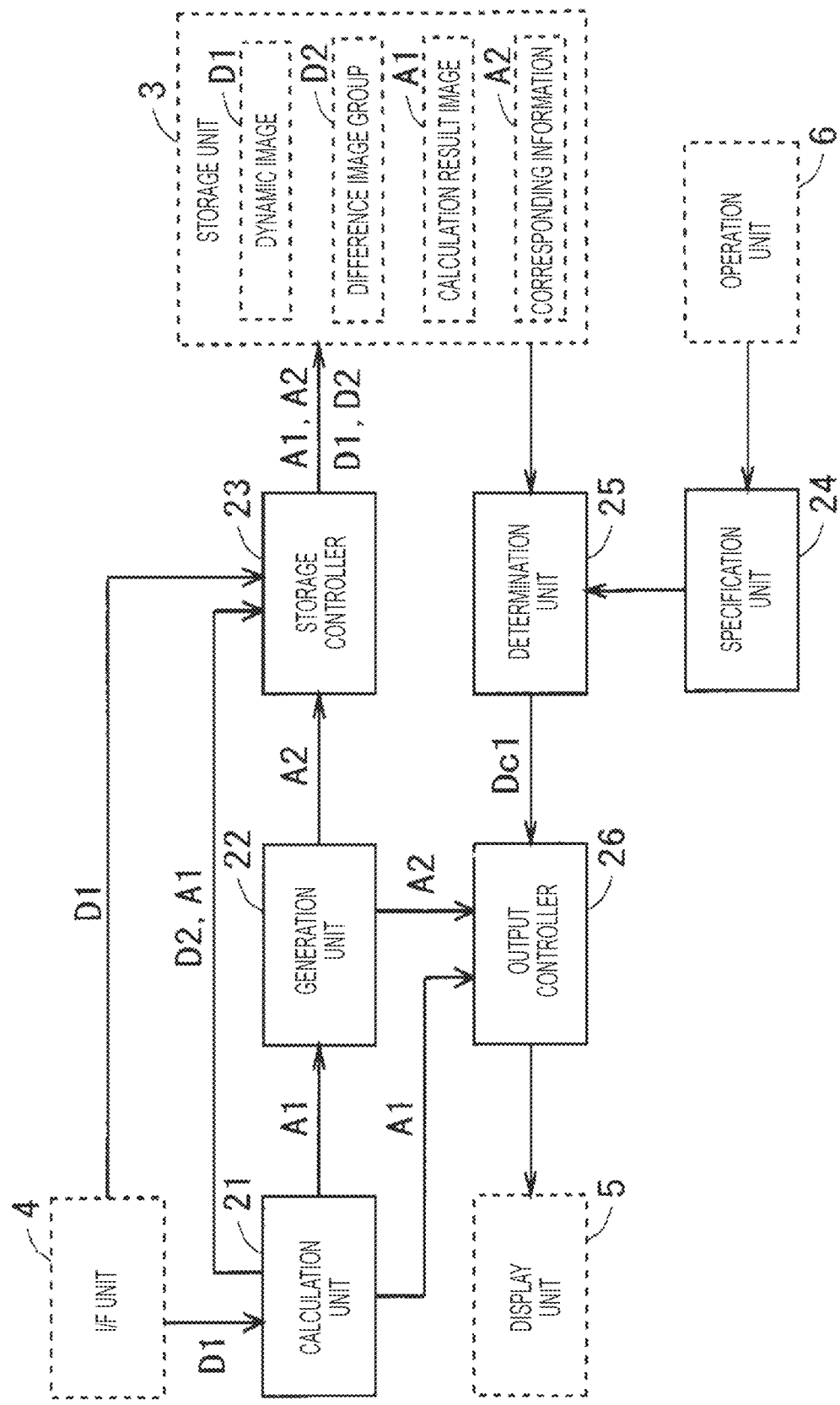
FIG. 2 is a block diagram of an exemplary functional structure according to diagnosis support processing.

FIG. 2 is a block diagram of an exemplary functional structure according to the diagnosis support processing realized by the controller 2. As illustrated in FIG. 2, the controller 2 includes a calculation unit 21, a generation unit 22, a storage controller 23, a specification unit 24, a determination unit 25, and an output controller 26 as the functional structure realized by the controller 2.

<(2-1) Calculation Unit>

The calculation unit 21 generates the calculation result image A1 (FIG. 5) by the calculation for the dynamic image D1 (FIG. 3). Each pixel value of the calculation result image A1 is the statistic obtained by the calculation for the dynamic image D1, for example.

FIG. 3 is a diagram of a plurality of exemplary frame images $F_n$ (n is a natural number of one to N) included in the dynamic image D1. In FIG. 3, the frame images $F_1$, $F_2$, $F_3$, . . . , and $F_N$ included in the medical dynamic image D1 for capturing the movement of a lung field as the object part are illustrated in the photographing order from the left. For example, the calculation unit 21 obtains the data of the dynamic image D1 from the modality 100 via the I/F unit 4.

Figure 4:
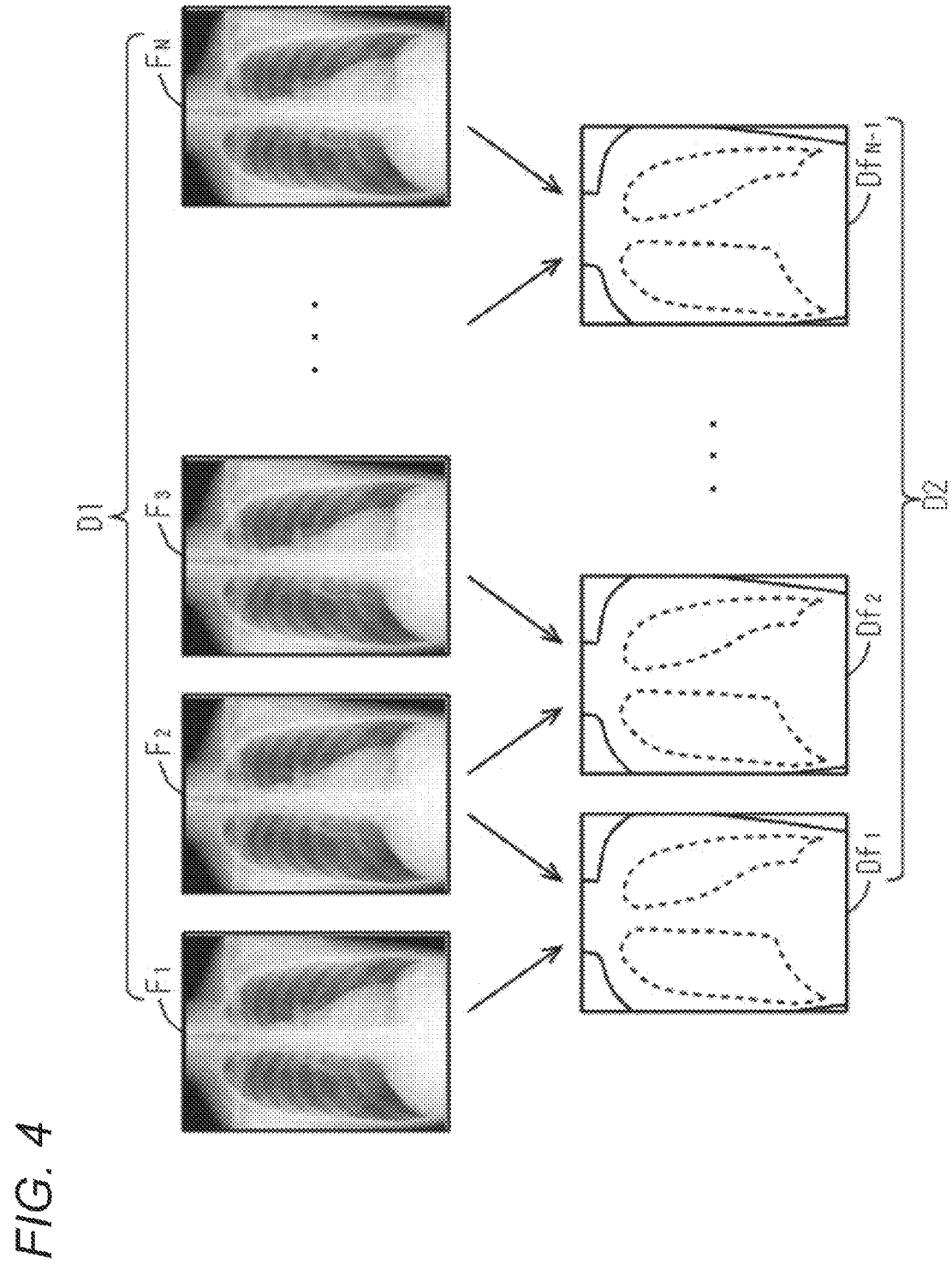
FIG. 4 is a diagram to describe an exemplary calculation for the dynamic image.
Figure 5:
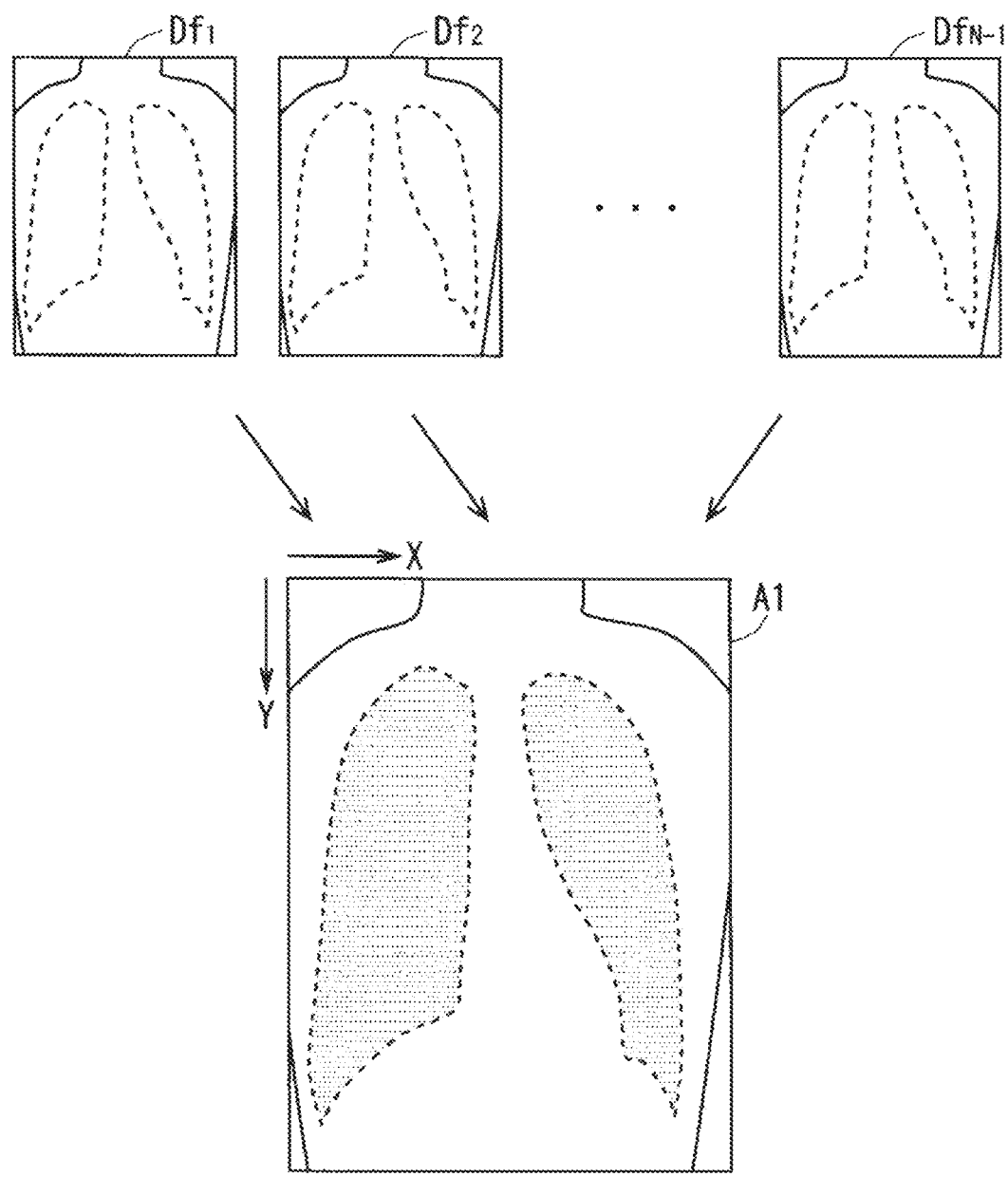
FIG. 5 is a diagram to describe an exemplary calculation for the dynamic image.

FIGS. 4 and 5 are diagrams to describe an exemplary calculation for the dynamic image D1.

For example, as illustrated in FIG. 4, between the frame images $F_m$ and $F_{m+1}$ (m is a natural number of one to N−1) of which the photographing orders are next to each other, the calculation unit 21 calculates an absolute value (referred to as a difference value) of the difference of the pixel values of the respective pixels. At this time, an m-th difference image $Df_m$ (m is a natural number of one to N−1) is generated from a m-th frame image $F_m$ and an m+1th frame image $F_{m+1}$ having the photographing orders next to each other. For example, a first difference image $Df_1$ is generated from a first frame image $F_1$ and a second frame image $F_2$, and a second difference image $Df_2$ is generated from the second frame image $F_2$ and a third frame image $F_3$. Accordingly, the difference images $Df_m$ of N−1 sheets are generated. It is assumed that the difference value regarding each pixel be the pixel value regarding each pixel. That is, a difference image group D2 including the difference images $Df_m$ of N−1 sheets is generated.

Before the difference image $Df_m$ is generated, processing for removing a noise may be performed relative to the dynamic image D1. The processing for removing the noise includes, for example, reduction processing, whole image emphasizing processing, and various filter processing relative to each frame image $F_n$, processing, in which a high-frequency component regarding the change of the pixel value in a time direction of each pixel is removed, relative to the dynamic image D1, and the like. Accordingly, the difference image $Df_m$ with little adverse effects caused by the noise may be generated.

Also, instead of calculating the difference value of the pixel value of each pixel, for example, the representative value of the pixel value according to a pixel block including two or more pixels is calculated. In addition, the difference value of the representative value of each pixel block is calculated so that the difference images $Df_m$ of N−1 sheets may be generated. Here, the statistic such as an average value and a median value of the pixel value may be employed as the representative value regarding the pixel block. With this aspect, the difference image $Df_m$ with little adverse effects caused by the noise may be generated.

An aspect that the difference images $Df_m$ of N−1 sheets are arranged in an order as the still images of N−1 sheets and displayed and an aspect that the difference images $Df_m$ of N−1 sheets are displayed as the dynamic image including the frame images $F_m$ of N−1 sheets can be considered. However, with these aspects, the doctor cannot look down at a whole analysis result about the function of the lung field and hardly performs the diagnosis.

The calculation unit 21 generates the image (calculation result image) A1 in which the difference images $Df_m$ of N−1 sheets are integrated into one sheet as illustrated in FIG. 5. Accordingly, the analysis result regarding the function of the lung field may be displayed in the aspect which is easily understood.

For example, processing is considered, in which the statistic of the pixel value is obtained for each small region which occupies the same position in each difference image $Df_m$ and the obtained value is mapped on a single image, as the processing for integrating the difference images $Df_m$ of N−1 sheets into one sheet of the calculation result image A1. Here, the small region may be one pixel and a pixel block including two or more pixels. As the statistic, for example, the representative value of the difference value such as the maximum value, the minimum value, the median value, and the like may be employed. The calculation result image A1 generated when the maximum value of the difference value is employed as the statistic is referred to as a MIP image.

For example, when an average value between the representative value and the pixel value regarding a few difference images which are before/after the difference image having the pixel value of the representative value as a reference in the photographing order is employed as the statistic regarding each small region, the calculation result image A1m with little adverse effects caused by the noise may be generated. Also, when the maximum value of the difference value in the small region is larger than a range of the residual value of the difference value in the small region as a reference by equal to or more than a predetermined amount or a predetermined ratio which have been previously set, the maximum value of the residual difference value in the small region except for the maximum value may be employed as the statistic of the small region. Even when this structure is employed, the calculation result image $A1_m$ with little adverse effects caused by the noise may be generated.

Also, the dynamic image D1 captures another region positioned around the lung field as the object part. Therefore, the calculation result image A1 may be generated in which a region (referred to as a lung field region) is recognized in which the lung field as the object part is captured from each frame image $F_n$, and in addition, in which the statistic obtained by the calculation for the lung field region is assumed to be each pixel value regarding the lung field region.

The calculation result image A1 generated by the calculation unit 21 as described above is visually output by the display unit 5 according to the control by the output controller 26. Accordingly, the doctor can look down at the whole analysis result about the function of the lung field and can roughly grasp abnormality in the function of the lung field.

<(2-2) Generation Unit>

The generation unit 22 corresponds the image in which the pixel value is employed when the statistic regarding one pixel region is obtained in the calculation by the calculation unit 21 relative to one pixel region for each region (referred to as a pixel region) including one or more pixels in the calculation result image A1. Here, the image in which the pixel value is employed when the statistic is obtained may include, for example, the frame image $F_n$ included in the dynamic image D1 and one or more images of the difference image $Df_m$ as a calculation middle image generated in the middle of the calculation by the calculation unit 21.

Accordingly, corresponding information A2 is generated. The corresponding information A2 is information for corresponding one or more images of the frame image $F_n$ and the difference image $Df_m$ relative to one pixel region for each pixel region regarding the calculation result image A1. In the frame image $F_n$ and the difference image $Df_m$, the pixel value is employed when the statistic regarding the pixel region is obtained by the calculation by the calculation unit 21. That is, when the calculation result image A1 is generated as the analysis result of the dynamic image D1 for capturing the object part of the living body, detailed information may be arranged. The analysis result has been obtained based on the detailed information.

In other words, in the corresponding information A2, it is indicated that the statistic has been obtained by employing the pixel value of which frame image $F_n$ and the pixel value of which difference image $Df_m$ and mapped relative to each pixel of the calculation result image A1 when the calculation result image A1 is generated by the calculation of the calculation unit 21.

Here, for example, for each pixel region in the calculation result image A1, when the pixel value (difference value) included in a single difference image $Df_m$ has been employed as it is as the statistic regarding a single pixel region, the single difference image $Df_m$ may correspond to the single pixel region. At this time, for example, the single pixel region may correspond to two frame images $F_n$ used to generate the single difference image $Df_m$ or one of the two frame images $F_n$. One of the two frame images $F_n$ may be determined according to a predetermined rule which has been previously set. For example, the predetermined rule is such that the frame images $F_n$ of an earlier/subsequent photographing order is employed.

Also, for example, for each pixel region in the calculation result image A1, when a value calculated from the pixel values (difference value) of two or more difference images $Df_m$ has been employed as the statistic regarding the single pixel region, the two or more difference images $Df_m$ may correspond to the single pixel region. At this time, for example, the single pixel region may correspond to one or more difference images $Df_m$ which is a part of the two or more difference images $Df_m$. The one or more difference images $Df_m$ which is a part of the two or more difference images $Df_m$ may be determined according to a predetermined rule which has been previously set. For example, the predetermined rule is such that the difference image $Df_m$ of an earlier/subsequent photographing order is employed.

Also, at this time, the single pixel region may correspond to the plurality of frame images $F_n$ used to generate the two or more difference images $Df_m$ or one or more frame images $F_n$ of the plurality of frame images $F_n$. The one or more frame images $F_n$ of the plurality of frame images $F_n$ may be determined according to a predetermined rule which has been previously set. For example, the predetermined rule is such that the frame image $F_n$ of an earlier/subsequent photographing order is employed.

FIG. 6 is a diagram to describe exemplary corresponding information A2. A situation is illustrated in FIG. 6 in which one pixel region of the calculation result image A1 corresponds to a frame image $F_1$, and another pixel region corresponds to a frame image $F_3$.

The correspondence of the images in the corresponding information A2 may be realized by, for example, that one or more channels are added to the data of each pixel region of the calculation result image A1 and information to specify the images (for example, frame number and the like) is described in the one or more channels. At this time, the calculation result image A1 and the corresponding information A2 may form integrated information. When a single pixel region corresponds to two or more images, for example, two or more channels are added to the data of the single pixel region.

Also, for example, an image having the same size as the calculation result image A1 is prepared, and information to specify one or more images is described as the data of each pixel of the image. Accordingly, the correspondence of the images in the corresponding information A2 may be realized. In addition, for example, the correspondence of the images in the corresponding information A2 may be realized by a table, in which the information for specifying the image is corresponded relative to a coordinate value of each pixel of the calculation result image A1, and the like.

The dynamic image D1 captures the other region positioned around the lung field as the object part. Therefore, the corresponding information A2 may be generated by corresponding one or more images relative to each pixel region in a region corresponding to the lung field (referred to as a lung field corresponding region) in the calculation result image A1. At this time, an aspect may be employed in which singular information is corresponded relative to a region other than the lung field corresponding region in the corresponding information A2. The singular information can be distinguished from the information for specifying the image (for example, a frame number).

<(2-3) Storage Controller>

The storage controller 23 causes the storage unit 3 to store the data of the dynamic image D1 input from the I/F unit 4, the data of the difference image group D2 and the calculation result image A1 generated by the calculation unit 21, and the corresponding information A2 generated by the generation unit 22. That is, the storage unit 3 has a configuration which can store the respective data of the dynamic image D1, the difference image group D2, the calculation result image A1, and the corresponding information A2.

<(2-4) Specification Unit>

The specification unit 24 specifies one or more pixel regions in the calculation result image A1 in response to the operation of the operation unit 6 by the doctor. Accordingly, a region to which the doctor pays attention (referred to as an attention region) may be specified.

FIGS. 7 and 8 are diagrams of an exemplary situation where an attention region Pa0 is specified in the calculation result image A1. As illustrated in FIGS. 7 and 8, for example, an aspect can be considered in which the attention region Pa0 is specified while a mouse pointer Mp1 is appropriately moved on the calculation result image A1 in response to the operation of the operation unit 6. For example, the attention region Pa0 specified by the specification unit 24 may be a region including one pixel region as illustrated in FIG. 7. Also, the attention region Pa0 may be a region including two or more pixel regions as illustrated in FIG. 8. The attention region Pa0 including two or more pixels may be specified by moving the mouse while pushing the left button from a start position to an end position. For example, it is assumed that a point on the upper left of the attention region Pa0 be the specified start position and a point on the lower right of the attention region Pa0 be the specified end position.

Also, for example, the specification unit 24 may specify one or more pixel regions in the calculation result image A1 in response to the operation of the operation unit 6 by the doctor. The one or more pixel regions correspond to at least one pixel region specified in the other image which is different from the calculation result image A1. Accordingly, one or more pixel regions in the calculation result image A1 may be easily specified. Here, the other image may include the difference image $Df_m$ generated by the generation unit 22. Also, the other image may include any one of the still image, the dynamic image, and the calculation result image regarding the dynamic image in which the object part which is the same as that captured by the dynamic image D1 is captured.

Accordingly, one or more pixel regions may be easily specified between the images in which the lung fields are captured as the same object part at different times. This aspect is extremely effective for confirming a difference between the current image and the image in the past, for example, when the position occupied by the object part in the image in the past matches with the position occupied by the object part in the current image. The processing for matching the positions with each other which are occupied by the object part in the image in the past and the current image may be realized, for example, by corresponding the positions of the lung fields with each other detected by the processing such as edge extraction and template matching from the image in the past and the current image.

Also, as the still image and the dynamic image which are the other images, the image obtained by photographing the object part as an object which is the same as that of the dynamic image D1 at a different time from that of the dynamic image D1 may be employed. In this case, for example, when at least a single pixel region is specified relative to the dynamic image or the still image used when the diagnosis has been performed in the past, an aspect is considered in which the single pixel region is used and specified as one or more pixel regions in the calculation result image A1. Also, as the calculation result image regarding the dynamic image as the other image, for example, an image in which the statistics obtained by the calculation for the dynamic image is assumed as the respective pixel values may be employed similarly to the processing for generating the calculation result image A1 by the calculation unit 21.

<(2-5) Determination Unit>

The determination unit 25 determines one or more output images Dc1, for example, based on one or more images corresponding to one or more pixel regions specified by the specification unit 24 in the corresponding information A2.

For example, when the single pixel region is specified by the specification unit 24 as illustrated in FIG. 7, it is determined that the single image is the output image Dc1 in a case where the single pixel region corresponds to the single image in the corresponding information A2. On the other hand, when the single pixel region specified by the specification unit 24 corresponds to two or more images in the corresponding information A2, it may be determined that the two or more images be the output image Dc1. It may be determined that one of the two or more images be the output image Dc1. For example, an image which has an order of photographing time relatively close to the center of the two or more images may be the output image Dc1.

On the other hand, for example, the attention region Pa0 specified by the specification unit 24 includes two or more pixel regions as illustrated in FIG. 8, a case is expected where the two or more pixel regions correspond to two or more images in the corresponding information A2.

Therefore, the determination unit 25 determines that the image which is a part of the two or more images corresponding to the two or more pixel regions in the corresponding information A2 is one or more output images Dc1, for example, in response to that the two or more pixel regions in the calculation result image A1 is specified by the specification unit 24. Here, the one or more output images Dc1 may be determined based on a determination rule which has been previously set. Accordingly, the output image Dc1 can be obtained while appropriately narrowing detailed information about the analysis result of the dynamic image D1 for capturing the lung field as the object part of the living body.

As the determination processing of the one or more output images Dc1 based on the determination rule, for example, the following processing may be considered. For example, the representative value regarding the frequency corresponding to each image of the two or more images relative to the two or more pixel regions specified by the specification unit 24 in the corresponding information A2 is calculated. Then, it is determined that one or more images of the two or more images according to the representative value be the output image Dc1. Accordingly, the detailed information can be easily obtained. The detailed information has a large effect when the analysis result of the dynamic image D1 for capturing the lung field as the object part of the living body is generated. Here, the representative value may include, for example, any one of the maximum value, the average value, and the median value.

Here, first to third determining processing will be described in which it is determined that the image which is a part of the two or more images corresponding to two or more pixel regions specified by the specification unit 24 in the corresponding information A2 is one or more output images Dc1.

Figure 9:
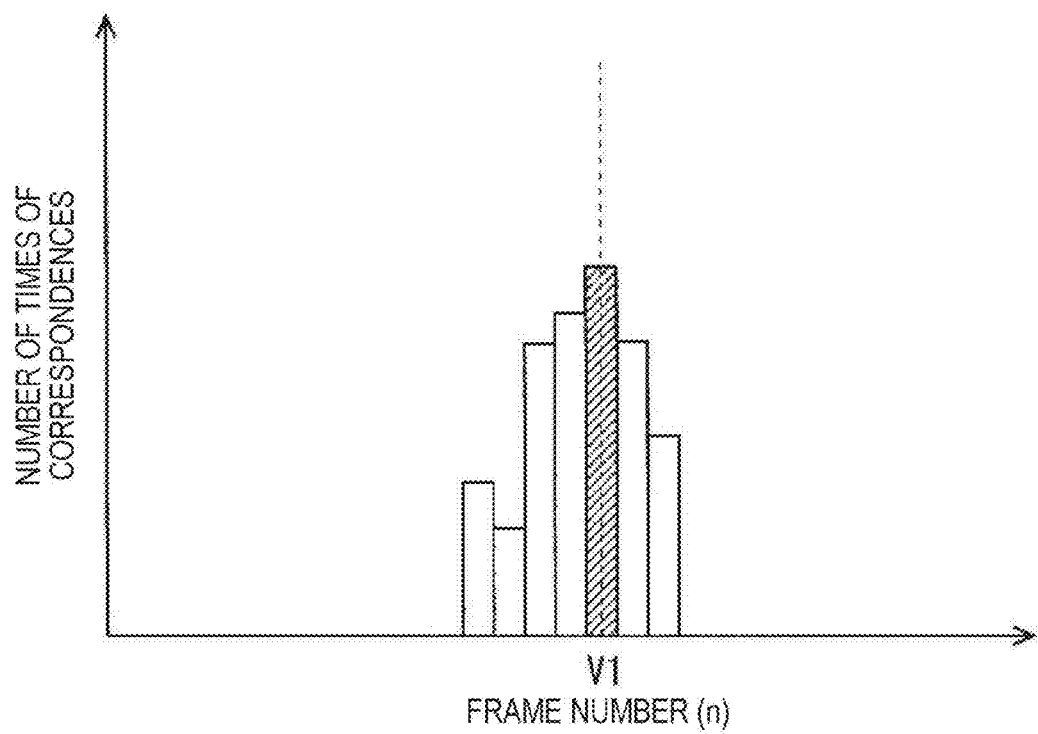
FIG. 9 is a diagram to describe first determining processing of an output image.
Figure 10:
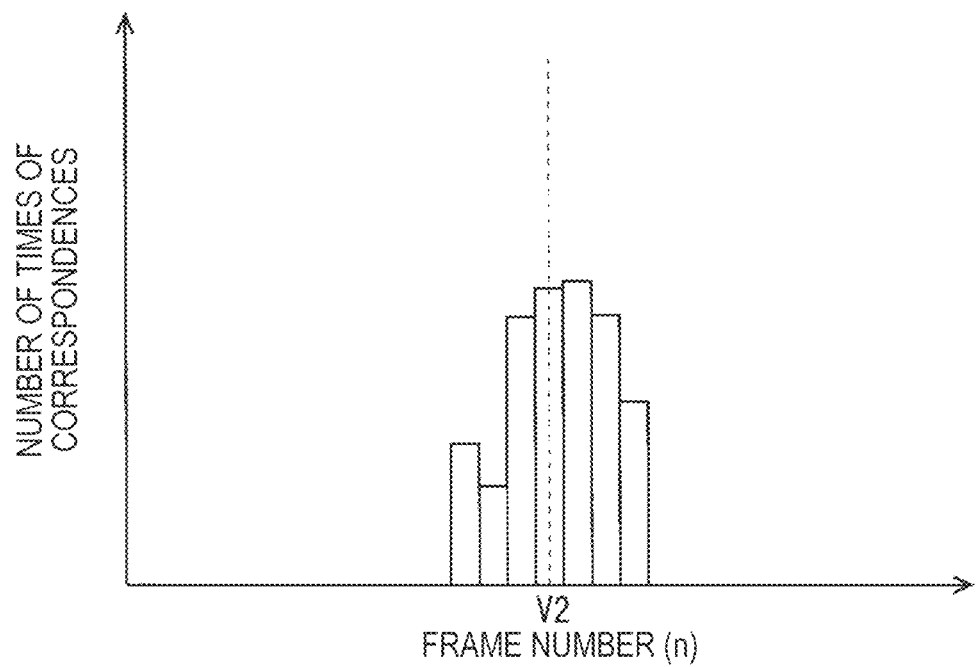
FIG. 10 is a diagram to describe second determining processing of an output image.
Figure 11:
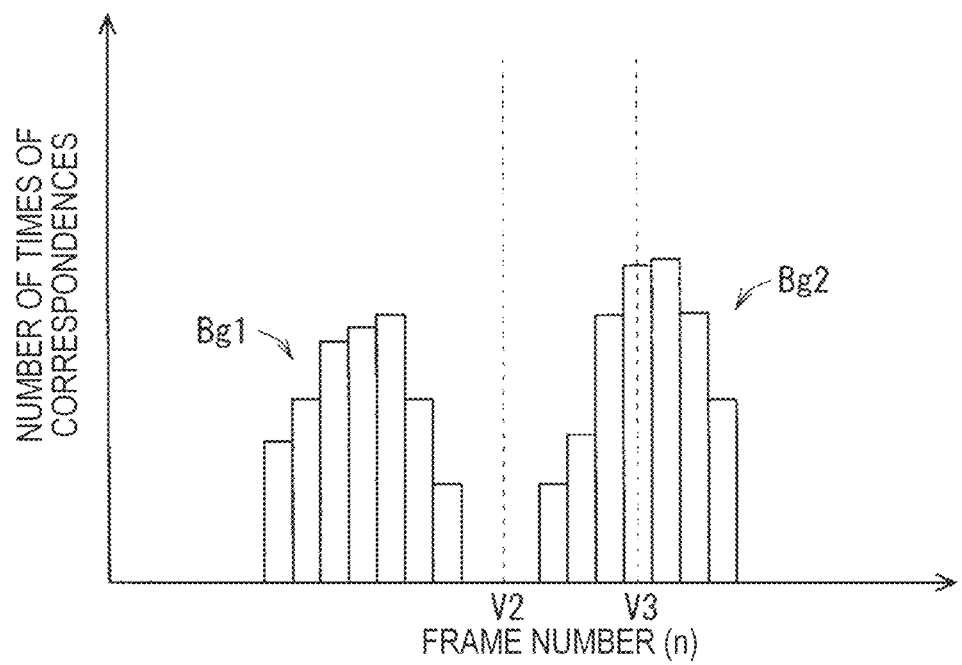
FIG. 11 is a diagram to describe third determining processing of an output image.

FIG. 9 is a diagram to describe the first determining processing of the output image Dc1, and FIG. 10 is a diagram to describe the second determining processing of the output image Dc1. FIG. 11 is a diagram to describe the third determining processing of the output image Dc1. Here, an example will be described in which the two or more images corresponding to the two or more pixel regions specified by the specification unit 24 in the corresponding information A2 are two or more frame images $F_n$ including the dynamic image D1.

First, a histogram is generated which indicates a frequency in which each frame image $F_n$ of two or more frame images $F_n$ corresponds relative to two or more pixel regions specified by the specification unit 24 in the corresponding information A2.

In FIGS. 9 to 11, a horizontal axis indicates a frame number (n) corresponding to the photographing order to identify the frame image $F_n$, and a vertical axis indicates the number of times as the corresponding frequency (referred to as the number of times of correspondences). In FIGS. 9 to 11, the number of times of the correspondences relative to each frame number is indicated by the length of a bar of a rectangle in a longitudinal direction. In bar graph illustrated in FIGS. 9 to 11, it is indicated that the two or more pixel regions specified by the specification unit 24 correspond relative to the plurality of frame images $F_n$ in the corresponding information A2.

Here, it is assumed in the first determining processing that the representative value regarding the frequency be the maximum value. Therefore, as illustrated in FIG. 9, it is determined that the frame image $F_{V1}$ according to a frame number $V_1$ ($V_1$ is a natural number) in which the number of times of correspondence becomes the maximum value as the representative value is the output image Dc1.

It is assumed in the second determining processing that the representative value regarding the frequency be the average value. Specifically, it is assumed that the representative value regarding the frequency be the average value of the frame numbers (n) regarding the plurality of frame images $F_n$ corresponding to two or more pixel regions specified by the specification unit 24 in the corresponding information A2. Therefore, as illustrated in FIG. 10, it is determined that a frame image $F_{V2}$ according to an average value V2 of the frame numbers (n) of the plurality of frame images $F_n$ corresponding to the two or more pixel regions specified by the specification unit 24 in the corresponding information A2 is the output image Dc1. When the representative value regarding the frequency is the median value, the output image Dc1 is determined according to the processing similar to that of case where the representative value regarding the frequency is the average value. A case where the representative value regarding the frequency is the median value is a case where the representative value is the median value of the frame numbers (n) of the plurality of frame images $F_n$ corresponding to two or more pixel regions specified by the specification unit 24 in the corresponding information A2.

However, as illustrated in FIG. 11, a case can be considered where a group of two or more rectangular bars (referred to as an appearing region) Bg1 and Bg2 appears in the histogram. The appearing regions are respectively formed by a plurality of rectangular bars regarding continuous frame numbers. In this case, when the second determining processing is simply performed, a failure occurs in which it is determined that the frame image $F_{V2}$ regarding the frame number in which the number of times of correspondence is zero is the output image Dc1.

In the third determining processing, as illustrated in FIG. 11, one appearing region is selected from among two or more appearing regions Bg1 and Bg2, and it is determined that a frame image $F_{V3}$ according to a representative value V3 regarding the frequency in the selected single appearing region is the output image Dc1. Here, as the processing for selecting the single appearing region from among two or more appearing regions, for example, processing for automatically selecting the appearing region Bg2 from among the two or more appearing regions Bg1 and Bg2 may be employed. The appearing region Bg2 has the maximum total sum of the number of times of the correspondences. Also, an aspect can be considered in which the representative value regarding the frequency is, for example, the average value or the median value similarly to the second determining processing.

An aspect may be employed in which any one of the first to third determining processing is performed for each pixel region in one dynamic image D1 according to the rule which has been previously set or a rule which has been previously set by the user.

Also, the determination unit 25 may determine the output image Dc1 by the following processing when at least one frame image $F_n$ included in the dynamic image D1 is included in one or more images corresponding to one or more pixel regions specified by the specification unit 24 in the corresponding information A2. For example, processing can be considered in which the output image Dc1 includes at least one frame image $F_n$ and a frame image $F_n$ having the photographing time before/after at least one frame image $F_n$ included in the dynamic image D1. That is, the plurality of frame images $F_n$ may be determined as the one or more output images Dc1. The plurality of frame images $F_n$ includes at least one frame image $F_n$ corresponding to one or more pixel regions specified by the specification unit 24 in the corresponding information A2 and the frame image $F_n$ having the photographing time before/after the one frame image F.

The plurality of frame images $F_n$ may include, for example, at least one frame image $F_n$ and a few frame images $F_n$ having the photographing time before/after the at least one frame image F. When this aspect is employed, detailed information may be displayed in a visually recognized form, for example, in a case where one or more output images Dc1 are displayed in the mode of the moving image.

<(2-6) Output Controller>

The output controller 26 displays various images on the display unit 5 based on the data regarding various images. For example, the output controller 26 displays the calculation result image A1 generated by the calculation unit 21 on the display unit 5. Also, for example, one or more output images Dc1 determined by the determination unit 25 is visually output on the display unit 5 by the output controller 26. Here, the one or more output images Dc1 may be one or more frame images $F_n$ and may be one or more difference images $Df_m$ as one or more calculation middle images. Also, the one or more output images Dc1 may include both the one or more frame images $F_n$ and the one or more difference images $Df_m$.

Figure 12:
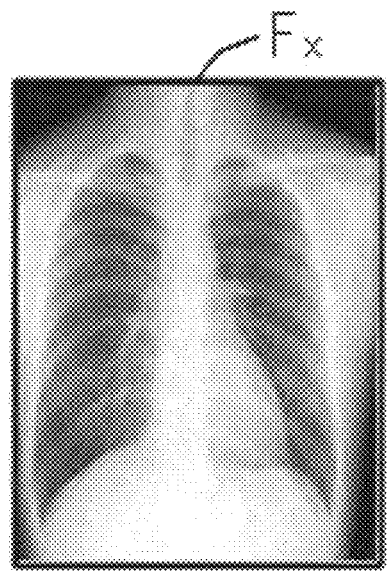
FIG. 12 is a diagram of a first display example for displaying an output image in a still image mode.
Figure 13:
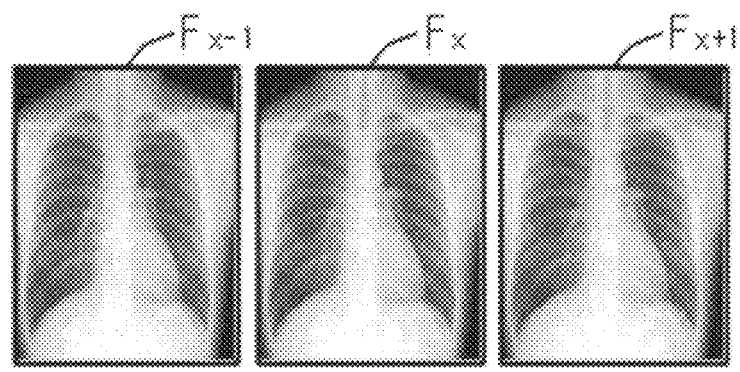
FIG. 13 is a diagram of a second display example for displaying an output image in a still image mode.

FIG. 12 is a diagram of a first display example in which a x-th frame image $F_x$ as the output image Dc1 included in the dynamic image D1 is displayed on the display unit 5 in a mode of the still image. Also, FIG. 13 is a diagram of a second display example in which x−1th frame image $F_{x-1}$ to x+1th frame image $F_{x+1}$ as the output image Dc1 included in the dynamic image D1 are displayed on the display unit 5 in the mode of the still image. As illustrated in FIGS. 12 and 13, one or more frame images $F_x$ as the output image Dc1 of a plurality of frame images $F_n$ (n=1 to N) included in the dynamic image D1 are selectively displayed.

Here, the one or more output images Dc1 corresponding to the attention regions to which the doctor pays attention and which is specified by the doctor in the calculation result image A1 are displayed. Accordingly, by looking at the calculation result image A1, the doctor can roughly grasp the abnormality in the function of the lung field by looking down the whole analysis result. In addition, one or more output images Dc1 as the detailed information may be easily and visually recognized. That is, the detailed information about the analysis result of the dynamic image D1 for capturing the object part of the living body can be easily and visually recognized.

Also, for example, when one or more output images Dc1 include one or more frame images $F_n$ included in the dynamic image D1, the one or more output images Dc1 may be displayed on the display unit 5 by the output controller 26 in at least one display mode of the following first and second display modes.

In the first display mode, one or more frame images $F_n$ as one or more output images Dc1 are displayed on the display unit 5 in a mode in which the frame images $F_n$ can be distinguished from the other image in the dynamic image D1 displayed in a mode of the moving image.

FIG. 14 is a diagram of a display example in which the x−1-th frame image $F_{x-1}$ to x+1-th frame image $F_{x+1}$ as the output image Dc1 are displayed in a mode in which they can be distinguished from the other frame image when the plurality of frame images $F_n$ is displayed in the mode of the moving image. As illustrated in FIG. 14, for example, an aspect can be considered in which various marks such as a thick frame is added to the frame images $F_{x-1}$ to $F_{x+1}$ as the output image Dc1. For example, the display mode of the frame images $F_{x-1}$ to $F_{x+1}$ as the output image Dc1 is set relatively different from that of the other frame image by changing a contrast, a color tone, and the like.

In the second display mode, one or more frame images $F_n$ as one or more output images Dc1 are displayed on the display unit 5 in a mode in which the frame images $F_n$ can be distinguished from the other frame image in the plurality of frame images $F_n$ included in the dynamic image D1 displayed in a mode of the still image. For example, an aspect can be considered in which the plurality of frame images $F_{n-3}$ to $F_{n+2}$ illustrated in FIG. 14 is concurrently displayed on the display unit 5 while being arranged and various marks such as the thick frame are added to the frame image $F_{x-1}$ to $F_{x+1}$ as the output image Dc1 of the plurality of frame images $F_{n-3}$ to $F_{n+2}$. Instead of adding the mark, for example, the display mode such as the contrast and the color tone may be relatively changed.

Figure 15:
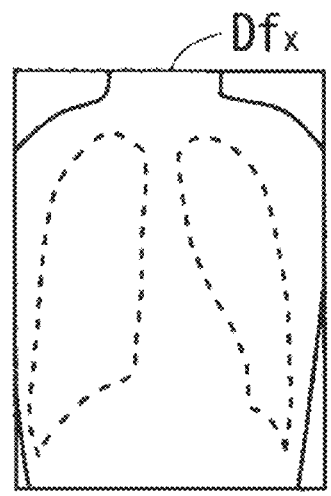
FIG. 15 is a diagram of a third display example for displaying an output image in a still image mode.
Figure 16:
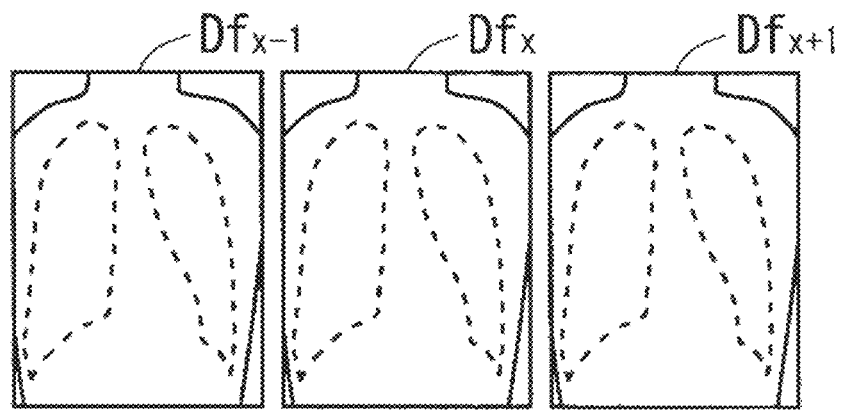
FIG. 16 is a diagram of a fourth display example for displaying an output image in a still image mode.

FIG. 15 is a diagram of a third display example in which the x-th difference image $Df_x$ as the output image Dc1 of the plurality of difference images $Df_m$ (m=1 to N−1) is displayed on the display unit 5 in the mode of the still image. Also, FIG. 16 is a diagram of a fourth display example in which a x−1-th difference image $Df_{x-1}$ to a x+1-th difference image $Df_{x+1}$ of the plurality of difference images $Df_m$ (m=1 to N−1) are displayed on the display unit 5 in the mode of the still image. As illustrated in FIGS. 15 and 16, one or more difference images $Df_x$ as the output image Dc1 of the plurality of difference images $Df_m$ (m=1 to N−1) are selectively displayed.

Also, for example, when one or more output images Dc1 include the difference images $Df_m$ as one or more calculation middle images, one or more output images Dc1 may be displayed on the display unit 5 by the output controller 26 in at least one display mode of the third and fourth display modes below.

In the third display mode, one or more difference images $Df_m$ as one or more output images Dc1 are displayed on the display unit 5 in a mode in which the difference images $Df_m$ can be distinguished from the other difference image in the plurality of difference images $Df_m$ to be displayed in the mode of the moving image.

FIG. 17 is a diagram of a display example in which the x−1-th difference image $Df_{x-1}$ to the x+1-th difference image $Df_{x+1}$ as the output image Dc1 are displayed in a mode in which they can be distinguished from the other difference image when the plurality of difference images $Df_m$ is displayed in the mode of the moving image. As illustrated in FIG. 17, an aspect can be considered in which, for example, various marks such as the thick frame are added to the difference images $Df_{x-1}$ to $Df_{x+1}$ as the output image Dc1. Instead of adding the mark, for example, the display mode such as the contrast and the color tone may be relatively changed.

In the fourth display mode, one or more difference images $Df_m$ as one or more output images Dc1 are displayed on the display unit 5 in a mode in which the difference images $Df_m$ can be distinguished from the other difference image $Df_m$ in the plurality of difference images $Df_m$ to be displayed in the mode of the still image. For example, an aspect can be considered in which the plurality of difference images $Df_{n-3}$ to $Df_{n+2}$ illustrated in FIG. 17 is concurrently displayed on the display unit 5 while being arranged and various marks such as the thick frame are added to the difference images $Df_{x-1}$ to $Df_{x+1}$ as the output image Dc1 of the plurality of difference images $Df_{n-3}$ to $Df_{n+2}$. Instead of adding the mark, for example, the display mode such as the contrast and the color tone may be relatively changed.

One or more display modes of the abovementioned first to fourth display modes are employed, and accordingly, the detailed information regarding the analysis result of the dynamic image for capturing the object part of the living body may be more easily and visually recognized.

<(3) Operational Flow Of Diagnosis Support Processing>

Figure 18:
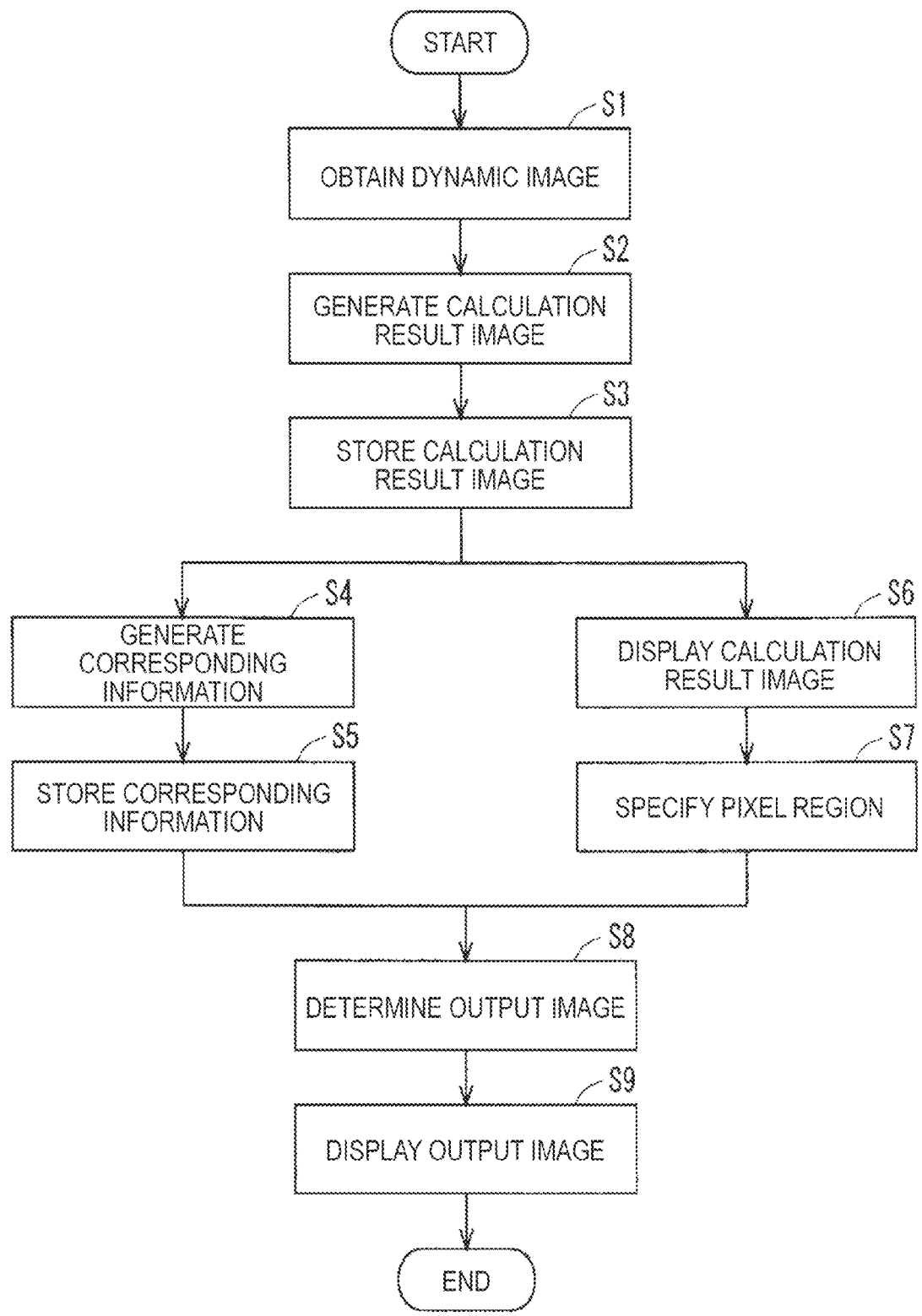
FIG. 18 is a flowchart of an exemplary operational flow according to the diagnosis support processing.

FIG. 18 is a flowchart of an exemplary operational flow according to the diagnosis support processing performed by the image processing apparatus 1. The present operational flow is realized by, for example, the controller 2 for executing the program Pg1. Here, the diagnosis support processing starts according to the operation of the operation unit 6 by the user, and processing of steps S1 to S9 is performed.

The controller 2 obtains the dynamic image D1 from the modality 100 via the I/F unit 4 in step S1. At this time, the data of the dynamic image D1 is input to the calculation unit 21, and at the same time, the data of the dynamic image D1 is stored in the storage unit 3 by the storage controller 23.

The calculation result image A1 is generated by the calculation unit 21 based on the dynamic image D1 in step S2.

The data of the calculation result image A1 generated in step S2 is stored in the storage unit 3 by the storage controller 23 in step S3.

In step S4, the generation unit 22 generates the corresponding information A2 regarding the calculation result image A1 generated in step S2.

The corresponding information A2 generated in step S4 is stored in the storage unit 3 by the storage controller 23 in step S5.

The calculation result image A1 generated in step S2 is displayed on the display unit 5 by the output controller 26 in step S6.

One or more pixel regions in the calculation result image A1 are specified by the specification unit 24 in response to the operation of the operation unit 6 by the doctor in step S7.

The determination unit 25 determines one or more output images Dc1 based on one or more images corresponding to one or more pixel regions specified in step S7 in the corresponding information A2 in step S8.

The one or more output images Dc1 determined in step S8 are displayed on the display unit 5 by the output controller 26 in step S9.

<(4) Summary>

As described above, in the image processing apparatus 1 according to the embodiment, the calculation result image A1 having the statistic obtained by the calculation for the medical dynamic image D1 as the pixel value is generated. At this time, the corresponding information A2 for corresponding to one or more images in which the pixel value is employed when the statistic is obtained is generated in each pixel region of the calculation result image A1. The output image Dc1 is determined based on one or more images corresponding to one or more pixel regions in response to specifying one or more pixel regions of the calculation result image A1 by the doctor.

Accordingly, for example, in the diagnosis by using the dynamic image D1 by the doctor, the calculation result image A1 as the analysis result is displayed, and at the same time, the image may be displayed in which the pixel value is employed when the statistic of the attention region Pa0 in the calculation result image A1 is obtained. That is, detailed information can be easily obtained when the dynamic image D1 which captures the object part of the living body is analyzed. As a result, the doctor can refer to both the calculation result image A1 and the output image Dc1 as the detailed information which has been a basis of the calculation result image A1. By using the calculation result image A1, the doctor can look down the whole analysis result about the function of the lung field. Accordingly, the diagnosis by the doctor regarding the object part is supported, and inappropriate diagnosis hardly occurs.

<(5) Modifications>

The present invention is not limited to the abovementioned embodiment, and various changes, modifications, and the like may be made without departing from the scope of the present invention.

For example, the output image Dc1 is displayed on the display unit 5 in the image processing apparatus 1 in the abovementioned embodiment. However, the present invention is not limited to this. For example, the output image Dc1 is determined by the image processing apparatus 1, and a mode may be employed in which information indicating the output image Dc1 is stored in a storage medium by the output controller 26 or a mode may be employed in which the information indicating the output image Dc1 is transmitted to the other device. These aspects may occur, for example, when a plurality of doctors perform the diagnosis together and when the diagnosis is performed and the diagnosis result is written by using a plurality of apparatuses.

Also, the calculation result image A1 and the corresponding information A2 are generated in the image processing apparatus 1 in the abovementioned embodiment. However, the present invention is not limited to this. For example, the calculation result image A1 and the corresponding information A2 generated by another apparatus may be used in the image processing apparatus 1.

Also, each pixel value of the calculation result image A1 is the statistic regarding a difference of the pixel value between the frame images adjacent to each other in the abovementioned embodiment. However, the present invention is not limited to this. For example, each pixel value of the calculation result image A1 may be the statistic calculated without using the difference of the pixel value such as the maximum value, the minimum value, and the like of each pixel in the plurality of frame images $F_n$ (n=1 to N) included in the dynamic image D1.

Also, the modality 100 is the apparatus for taking the x-ray by using the FPD in the abovementioned embodiment. However, the present invention is not limited to this. For example, the modality 100 may be a medical imaging apparatus typified by the CT, the MRI, the ultrasonic diagnosis apparatus, and the like. The diagnosis support processing according to the abovementioned embodiment can be applied to, for example, processing in which the diagnosis is supported. The diagnosis is performed for a cross sectional image of a three-dimensional image obtained by the CT, the MRI, and the like.

Also, the lung field is exemplified as an exemplary object part in the abovementioned embodiment. However, the present invention is not limited to this. The object part may be, for example, other organs such as a brain and a heart. In this case, for example, a blood flow change in the organ can be considered as a target of the analysis in the object part.

Also, the diagnosis support processing by using the medical dynamic image D1 is performed in the abovementioned embodiment. However, the present invention is not limited to this. For example, the dynamic image D1 is not limited to the medical image and may be a dynamic image used for other purposes such as a dynamic image for simply analyzing various functions of the living body. At this time, the user of the image processing apparatus 1 is not limited to the doctor and may be various users such as a researcher and an operator.

Also, the living body includes various animals including humans and the like in the embodiment. However, the living body is not limited to the above. The living body may include, for example, other living things such as plants.

Also, the object part exists in the living body in the abovementioned embodiment. However, the present invention is not limited to this, and the object part may be other parts of the living body such as a surface of the living body. At this time, a change of temperature distribution on the surface of the body and the like may be the target of the analysis. Also, the object part is not limited to the part of the living body. For example, the object part may be parts included in a part of various objects including an inorganic matter such as an industrial product and manufacturing facilities.

Also, one or more pixel regions in the calculation result image A1 are specified by the specification unit 24 in response to the operation of the operation unit 6 by the user in the abovementioned embodiment. However, the present invention is not limited to this. For example, one or more pixel regions in the calculation result image A1 may be automatically specified by the specification unit 24 according to a predetermined rule which has been previously set. Here, for example, an aspect is considered in which the pixel regions in the calculation result image A1 for satisfying a predetermined condition which has been previously set are automatically specified as the one or more pixel regions. For example, when each pixel value of the calculation result image A1 is the maximum value regarding the absolute value (difference value) of the difference between the pixel values of the respective pixels in the frame images having the photographing orders next to each other, a condition that the pixel value is less than a predetermined threshold and the like may be employed as the predetermined condition. Also, for example, one or more pixel regions in the calculation result image A1 may be automatically specified by the specification unit 24. The one or more pixel regions correspond to at least one pixel region specified in the other image which is different from the calculation result image A1. When at least one pixel region in the other image which is different from the calculation result image A1 is specified, at least one pixel region in the other image may be automatically specified according to a predetermined rule which has been previously set.

Also, the instruction signal is input according to the operation of the operation unit 6 by the user in the abovementioned embodiment. However, the present invention is not limited to this. For example, an aspect may be employed in which the voice is analyzed according to the input of the voice and the instruction signal is input. That is, various configuration may be employed in which the instruction signal is input according to an operation by the user.

It is obvious that all or a part of the abovementioned embodiment and various modifications can be appropriately combined within a range with no contradiction.

Although the present invention has been described and illustrated in detail, it is clearly understood that the same is by way of illustrated and example only and is not to be taken by way of limitation, the scope of the present invention being interpreted by terms of the appended claims.

What is claimed is:
1. An image processing apparatus comprising:
   a storage unit comprising a structure that stores corresponding information, wherein the corresponding information is previously generated as follows:
      taking a dynamic image of an object that comprises a total number n of sequential frame images $F_n$, wherein n =2,3, . . . n;
      generating a calculation middle image formed from a plurality of the frame images;
      integrating the calculation middle image into a single calculation result image by obtaining for each pixel of the calculation middle image a statistic value in a pixel region of each pixel and then mapping the statistic values into a corresponding pixel of the single calculation result image; and
      generating the corresponding information by determining information that corresponds each pixel region of the single calculation result image to one of the frame images $F_n$ or the calculation middle image of which a pixel value is employed in the mapping of the statistic value corresponding to the pixel region;
   a specification unit comprising a structure that specifies one of the pixel regions in the single calculation result image; and a determination unit comprising a structure that determines an output image based on the corresponding information corresponding to the pixel region specified by the specification unit.

2. The image processing apparatus according to claim 1, further comprising:
a calculation unit comprising a structure that generates the calculation result image via the calculation for the dynamic image; and
a generation unit comprising a structure that generates the corresponding information.

3. The image processing apparatus according to claim 1, still further comprising: an output controller comprising a structure that makes a display unit visually output the output image determined by the determination unit.

4. The image processing apparatus according to claim 3, wherein the output controller makes the display unit display a first frame image corresponding to the output image so as to be distinctive from a second frame image that is different from the output image, when the first frame image comprises the output image, homologized by the corresponding information, being displayed as a moving image.

5. The image processing apparatus according to claim 3, wherein the output controller makes the display unit display a first frame image corresponding to the output image so as to be distinctive from a second frame image that is different from the output image, when the first frame image comprises the output image, homologized by the corresponding information, being displayed as a static image.

6. The image processing apparatus according to claim 3, wherein the output controller makes the display unit display a first calculation middle image corresponding to the output image so as to be distinctive from a second calculation middle image that is different from the output image, when the first calculation middle image comprises the output image, homologized by the corresponding information, being displayed as a moving image.

7. The image processing apparatus according to claim 3, wherein the output controller makes the display unit display a first calculation middle image corresponding to the output image so as to be distinctive from a second calculation middle image that is different from the output image, when the first calculation middle image comprises the output image, homologized by the corresponding information, being displayed as a static image.

8. The image processing apparatus according to claim 1, wherein the determination unit determines that an image that is a part of two or more images corresponding to two or more pixel regions in the corresponding info nation is the output image based on a determination rule, which has been previously set in response to two or more pixel regions in the single calculation result image having been specified by the specification unit.

9. The image processing apparatus according to claim 8, wherein the determination unit 1) calculates a representative value regarding a frequency in which the respective images of the two or more images that correspond relative to the two or more pixel regions in the corresponding information based on the determination rule and 2) determines an image according to the representative value from among the two or more images as the output image.

10. The image processing apparatus according to claim 9, wherein the representative value includes any one of a maximum value, an average value, and a median value of a field of the calculation middle image at a position that corresponds to a position of the pixel region of the single calculation result image.

11. The image processing apparatus according to claim 1, wherein the specification unit specifies each pixel region corresponding to at least one pixel region specified in an image other than the single calculation result image.

12. The image processing apparatus according to claim 11, wherein the image other than the single calculation result image includes anyone of the images of a still image, a dynamic image, and the single calculation result image having the statistic obtained by the calculation for the dynamic image as each pixel value, and the still image, the dynamic image, and the single calculation result image capture the same object part as the object captured in the dynamic image.

13. The image processing apparatus according to claim 1, wherein the output image determined by the determination unit comprises a plurality of frame images that comprises 1) one of the frame images $F_n$ and 2) a second one of the frame images $F_n$ that is before/after the one of the frame images $F_n$.

14. A non-transitory recording medium storing a computer readable program, wherein the program causes the image processing apparatus to function as the image processing apparatus according to claim 1 by being executed by a processor included in the image processing apparatus.

* * * * *